(12) United States Patent
Argentine et al.

(10) Patent No.: US 9,642,696 B2
(45) Date of Patent: May 9, 2017

(54) DILATATION TESTER FOR A STENT-GRAFT PROSTHESIS

(71) Applicant: Medtronic Vascular, Inc., Santa Rosa, CA (US)

(72) Inventors: Jeffery Argentine, Petaluma, CA (US); Mark Rowe, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 95 days.

(21) Appl. No.: 14/691,109

(22) Filed: Apr. 20, 2015

(65) Prior Publication Data
US 2016/0302912 A1 Oct. 20, 2016

(51) Int. Cl.
*G01N 3/12* (2006.01)
*A61F 2/07* (2013.01)
*G01N 21/552* (2014.01)
*G01N 30/74* (2006.01)
*G01N 3/34* (2006.01)
G01N 21/3504 (2014.01)
G01N 21/03 (2006.01)
G01N 21/65 (2006.01)
G01N 30/60 (2006.01)

(52) U.S. Cl.
CPC .............. *A61F 2/07* (2013.01); *G01N 3/12* (2013.01); *G01N 3/34* (2013.01); *G01N 21/552* (2013.01); *G01N 30/74* (2013.01); *A61F 2240/008* (2013.01); *G01N 21/0332* (2013.01); *G01N 21/3504* (2013.01); *G01N 21/658* (2013.01); *G01N 30/6082* (2013.01); *G01N 2203/0007* (2013.01); *G01N 2203/0037* (2013.01); *G01N 2203/0073* (2013.01); *G01N 2203/0089* (2013.01)

(58) Field of Classification Search
USPC ....................................... 73/37, 824
See application file for complete search history.

(56) References Cited

U.S. PATENT DOCUMENTS

| | | | |
|---|---|---|---|
| 6,510,722 B1 * | 1/2003 | Ching | A61F 2/958 29/282 |
| 8,006,568 B2 * | 8/2011 | Halderman | G01N 3/04 73/818 |
| 2003/0070469 A1 * | 4/2003 | Kokish | A61F 2/958 72/402 |
| 2004/0016301 A1 * | 1/2004 | Moreno | G01N 3/32 73/849 |

(Continued)

*Primary Examiner* — Harshad R Patel
*Assistant Examiner* — Monica S Young (57) ABSTRACT

A dilatation or fatigue tester for a stent-graft prosthesis includes a sample holder having a compressible member that defines a chamber for receiving a stent-graft prosthesis in an expanded state, a bearing assembly disposed to contact and act on an exterior surface of the compressible member of the sample holder, and an actuation assembly operably coupled to the bearing assembly for rotating the bearing assembly relative to the sample holder. Rotation of the bearing assembly cyclically compresses the compressible member of the sample holder to thereby provide cyclical radial loading and unloading of a stent-graft prosthesis received therein for simulating physiologic loading conditions of a stent-graft prosthesis within a vasculature due to a beating heart.

20 Claims, 10 Drawing Sheets

(56) References Cited

U.S. PATENT DOCUMENTS

| | | | | |
|---|---|---|---|---|
| 2010/0242620 A1* | 9/2010 | Lorenz | ................ | A61F 2/82 |
| | | | | 73/856 |
| 2010/0291524 A1* | 11/2010 | Iwasaki | ................ | G01N 3/32 |
| | | | | 434/272 |
| 2011/0146385 A1* | 6/2011 | Weinberg | ................ | G01N 3/36 |
| | | | | 73/37 |

* cited by examiner

DILATATION TESTER FOR A STENT-GRAFT PROSTHESIS

FIELD OF THE INVENTION

The invention relates in general to stent-graft prostheses, and more particularly to a dilatation tester for a stent-graft prosthesis.

BACKGROUND OF THE INVENTION

Prostheses for implantation in blood vessels or other similar organs of the living body are, in general, well known in the medical art. For example, prosthetic endovascular grafts constructed of biocompatible materials have been employed to replace or bypass damaged or occluded natural blood vessels. Grafting procedures are also known for treating aneurysms. In general, endovascular grafts include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. In addition, the stents also have a patency function in that the stents keep the graft open and radially expanded along portions of the graft that are not necessarily opposed to the vessel wall, i.e., along portions of graft disposed within an aneurysm sac. Thus, endovascular grafts are typically held in place by mechanical engagement and friction due to the apposition forces provided by the radially expanded stents.

Stent-graft prostheses must be capable of withstanding the physiological dynamics that occur within the vessel or organ in which they are implanted. Thus, stent-graft prostheses must undergo testing to determine the fatigue limitations thereof. For example, the FDA currently requires medical device manufacturers of stent-graft prostheses to submit data to support the safety and efficacy of the permanent implant device. One required test data is the accelerated fatigue testing of stents or stent-graft prostheses. The FDA guidelines require ten years equivalent of test data, which translates to 400 million cycles of fatigue stress.

Devices for fatigue testers are usually hydraulic-based testing devices that force fluid within the lumen of a stent or stent-graft prosthesis in a pulsating fashion at a high frequency in order to simulate physiologic loading conditions, i.e., in order to simulate systolic and diastolic pressures. Such hydraulic-based testing devices operate at a maximum pulse frequency ranging between 1000-2000 cycles per minute, or approximately 16-33 Hz. In order to obtain the ten years equivalent of test data required by the FDA, such hydraulic-based testing devices must run continuously over a period of several months. Further, testing operation of such hydraulic-based devices must be closely monitored because pressure changes will change dilatation, thereby requiring the test to be restarted.

Hence, there is a need in the art for an improved fatigue tester that is configured to operate at higher frequencies for decreased testing times and/or that requires less monitoring during testing.

BRIEF SUMMARY OF THE INVENTION

Embodiments of the present invention are directed to a dilatation tester for a stent-graft prosthesis. The dilatation tester includes a sample holder having a compressible member that defines a chamber for receiving a stent-graft prosthesis in an expanded state, a bearing assembly disposed to contact an exterior surface of the compressible member of the sample holder, and an actuation assembly operably coupled to the bearing assembly for rotating the bearing assembly relative to the sample holder. Rotation of the bearing assembly causes cyclical compression of the compressible member of the sample holder to thereby provide cyclical loading and unloading of a stent-graft prosthesis received therein for simulating physiologic loading conditions of a stent-graft prosthesis within a vasculature due to a beating heart.

According to another embodiment hereof, the dilatation tester includes a sample holder having a compressible member that defines a chamber for receiving a stent-graft prosthesis in an expanded state, and an exterior surface of the compressible member defines a plurality of longitudinally-extending protuberances evenly spaced about a circumference of the compressible member. The dilatation tester also includes a bearing assembly including a plurality of needle roller bearings that surround and make contact with the exterior surface of the compressible member of the sample holder. The dilatation tester also includes an actuation assembly operably coupled to the bearing assembly for rotating the bearing assembly relative to the sample holder. Rotation of the bearing assembly causes cyclical compression of the compressible member when the plurality of needle roller bearings of the bearing assembly roll over and radially compress the plurality of longitudinally-extending protuberances of the compressible member of the sample holder to thereby provide cyclical radial loading and unloading of a stent-graft prosthesis received therein for simulating physiologic loading conditions of a stent-graft prosthesis within a vasculature due to a beating heart.

According to another embodiment hereof, the dilatation tester includes a sample holder having a compressible member that defines a chamber for receiving a stent-graft prosthesis in an expanded state, and an exterior surface of the compressible member defines a plurality of longitudinally-extending protuberances evenly spaced about a circumference of the compressible member. The dilatation tester also includes a bearing assembly including a plurality of needle roller bearings that surround and make contact with the exterior surface of the compressible member of the sample holder. The dilatation tester also includes an actuation assembly operably coupled to the bearing assembly for rotating the bearing assembly relative to the sample holder. The compressible member and a stent-graft prosthesis received therein are radially compressed when the plurality of longitudinally-extending protuberances of the compressible member are aligned with the plurality of needle roller bearings of the bearing assembly.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The following detailed description is merely exemplary in nature and is not intended to limit the invention or the application and uses of the invention. Although the description of the invention is in the context of testing stent-graft prosthesis devices, the invention may also be used to test other tubular prostheses where it is deemed useful. Furthermore, there is no intention to be bound by any expressed or implied theory presented in the preceding technical field, background, brief summary or the following detailed description.

Embodiments hereof relate to a dilatation or fatigue tester that mechanically and cyclically radially compresses a stent-graft prosthesis received therein in order to mimic or simulate physiologic loading conditions of a stent-graft prosthesis within a vasculature due to a beating heart. More particularly, "physiologic loading conditions" as used herein includes simulation of systolic and diastolic pressures within a vasculature due to a beating heart, with such pressures being simulated at accelerated frequencies. Systolic blood pressure is the highest pressure that occurs when the heart is contracting, which causes a rise or increase in blood pressure, while diastolic blood pressure is the lowest pressure between two heartbeats, which occurs when the heart is relaxed. Since the dilatation tester of the present invention achieves compression of the stent-graft prosthesis completely via mechanical means, the performance of the tester device is predictable in terms of motion and speed and thus does not need to be monitored. In addition, one complete rotation or turn of the dilatation tester radially compresses the stent-graft prosthesis received therein up to nine times, and the dilatation tester may operate at a frequency up to 150 Hz or 9000 cycles per minute. Further, the tester device allows a stent-graft prosthesis to be tested with up to 12% distention, with distention as used herein referring to the difference between the expanded and compressed diameters of the stent-graft prosthesis. Thus, the total time required to obtain the ten years equivalent of test data required by the FDA is significantly reduced as compared to other fatigue testers. In addition, since the tester device operates so much more quickly than known testers and is much less expensive to manufacture, the tester device can also be used during development of new stent-grafts, i.e., prototypes.

Figure 1:
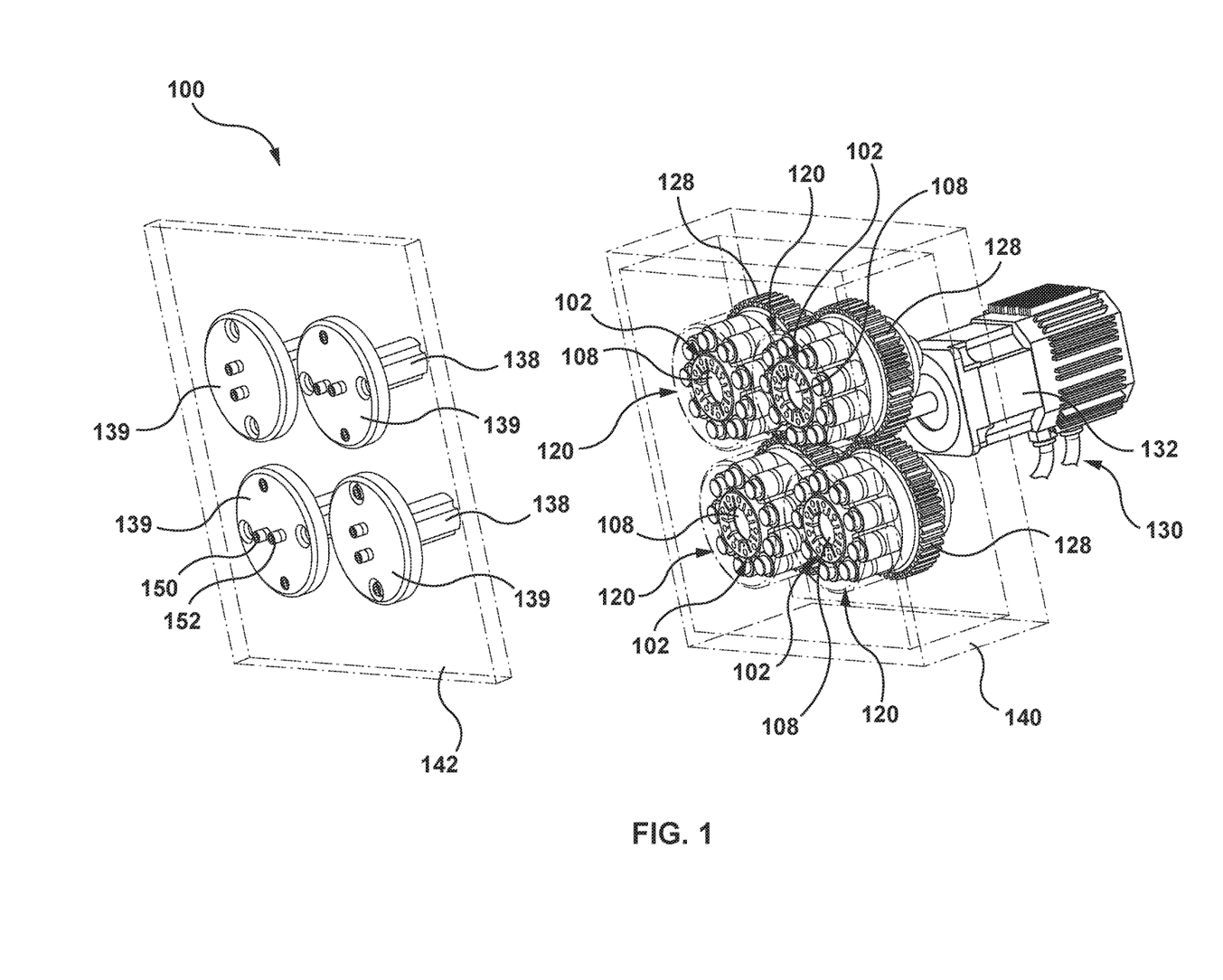
FIG. 1 is an exploded perspective view of a dilatation tester according to an embodiment hereof, wherein a cover of the dilatation tester is shown separated or removed from a housing of the dilatation tester.
Figure 2:
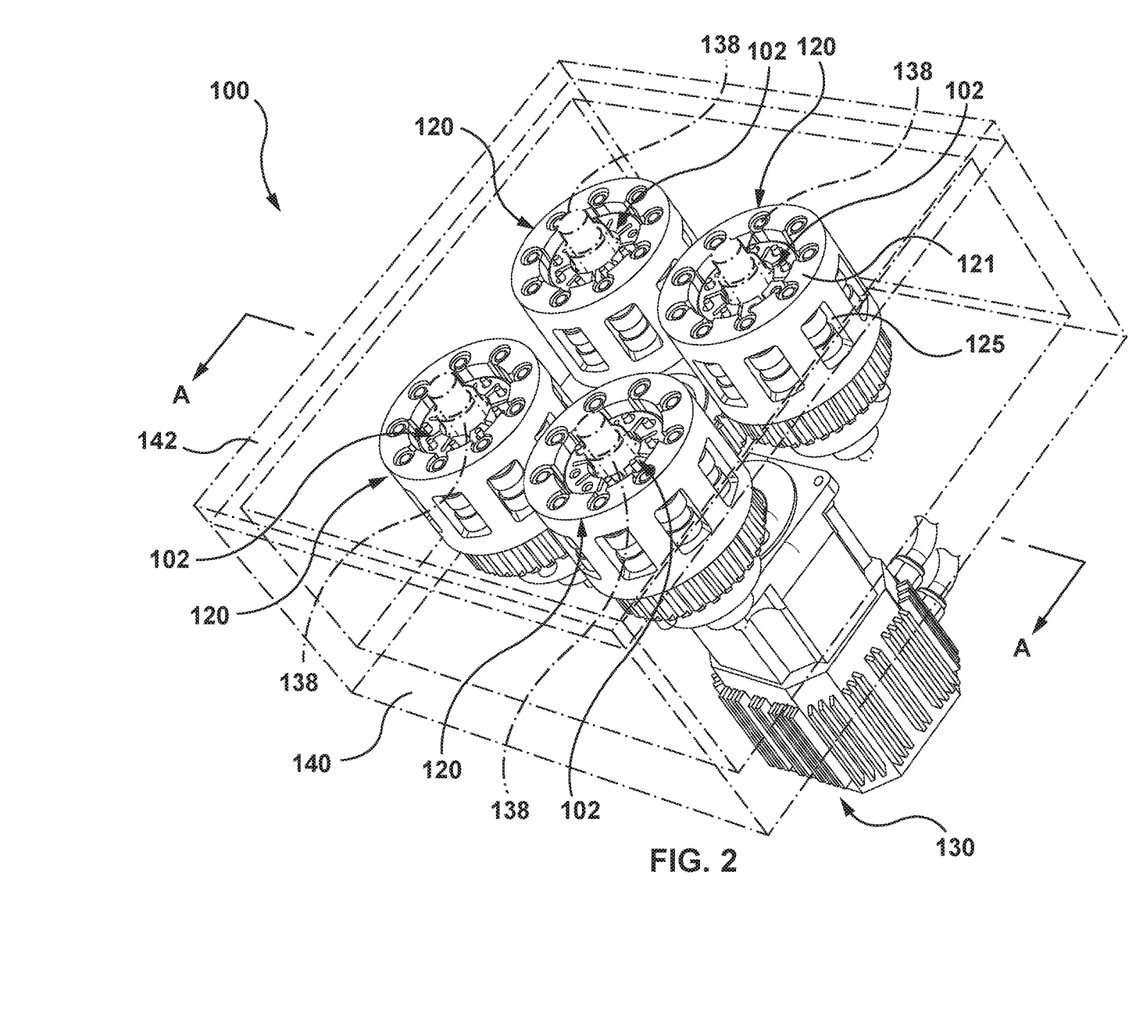
FIG. 2 is an assembled perspective view of the dilatation tester of FIG. 1, the cover of the dilatation tester being shown disposed over and secured to the housing of the dilatation tester, wherein heater caps of the cover are removed in FIG. 2 for illustration purposes only.

More particularly, with reference to FIGS. 1 and 2, a dilatation or fatigue tester 100 is shown in an exploded perspective view in FIG. 1 and an assembled perspective view in FIG. 2. In FIG. 1, a cover 142 is shown separated or removed from a housing 140 of dilatation tester 100 while in FIG. 2 cover 142 is shown sealingly coupled to the housing 140. Dilatation tester 100 includes at least one sample holder 102 that receives a stent-graft prosthesis 108 in an expanded state, a bearing assembly 120 that acts on sample holder 102, and an actuation assembly 130 that rotates bearing assembly 120 relative to sample holder 102 in order to provide cyclical radial compression of stent-graft prosthesis 108 received therein. A perspective view of stent-graft prosthesis 108 is shown in the exploded view of FIG. 4. As will be understood by one of ordinary skill in the art, stent-graft prosthesis 108 is a tubular component having a first end 164 and a second end 166 and includes a tubular graft 160 with at least one radially-compressible stent or scaffold 162 coupled to the tubular graft for supporting the graft material. Stent or scaffold 162 is operable to radially self-expand into apposition with an interior wall of a body vessel. In another embodiment hereof, stent or scaffold 162 is balloon-expandable. The cyclical radial compression and decompression of stent-graft prosthesis 108, which may also be considered cyclical loading and unloading of stent-graft prosthesis, mimics or simulates physiologic loading conditions of a stent-graft prosthesis implanted within a vasculature due to a beating heart in order to test stent-graft prosthesis 108 according to industry standards.

In the embodiment shown in the figures, dilatation tester 100 includes four sample holders 102 and four corresponding bearing assemblies 120 in order to simultaneously test four stent-graft prostheses 108. Stated another way, dilatation tester 100 includes an equal number of bearing assemblies and corresponding sample holders. Sample holders 102 of dilatation tester 100 are identical in structure and bearing assemblies 120 of dilatation tester 100 are also identical in structure. As will be understood by those of ordinary skill in the art, dilatation tester 100 may be modified to include fewer or greater than the four sample holders and corresponding bearing assemblies shown in the figures, such as one of each, without departing from the scope hereof.

Figure 3:
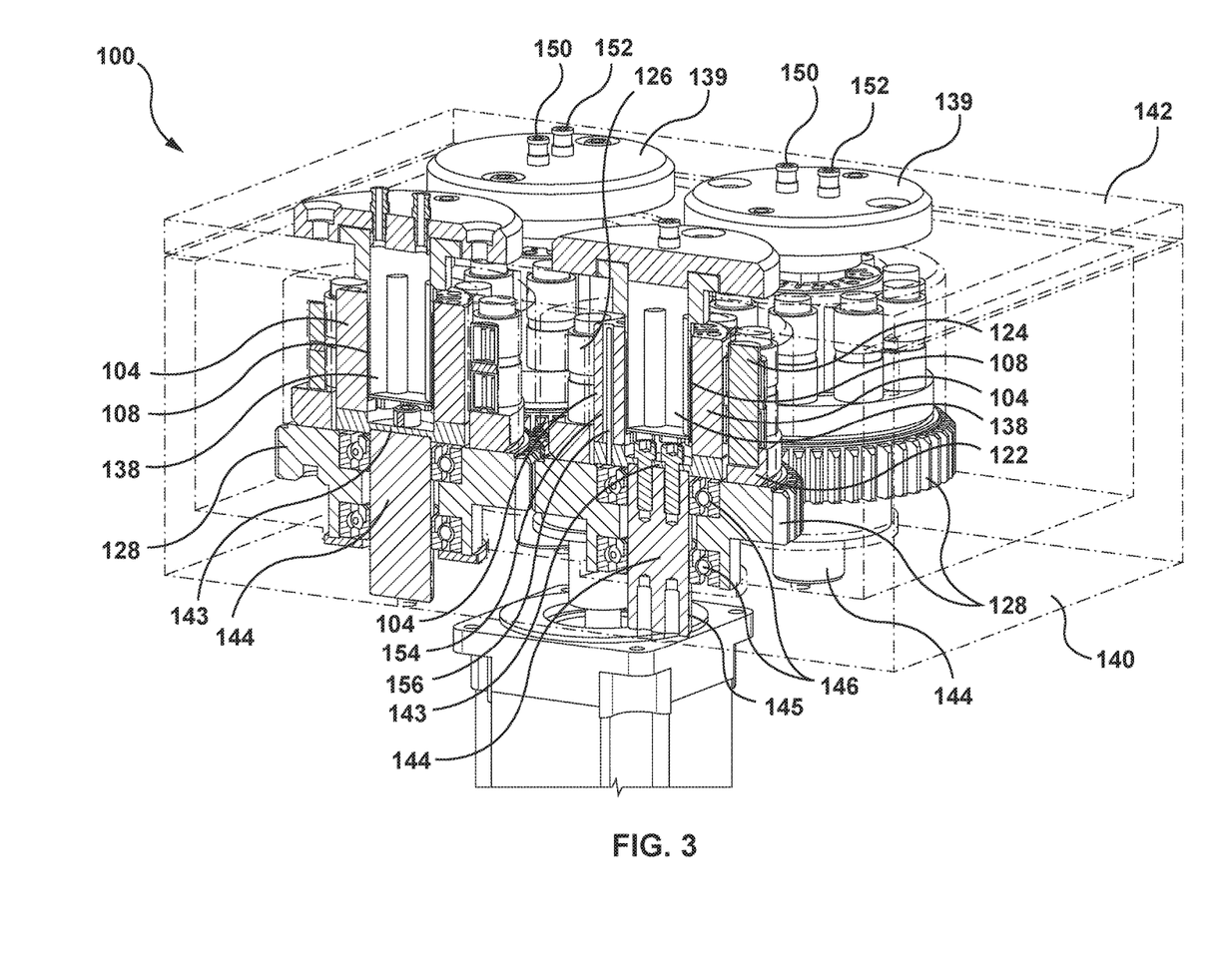
FIG. 3 is a cross-sectional view of FIG. 2 taken along a line A-A thereof, wherein heater caps of the cover are shown in FIG. 3.

Sample holders 102 and bearing assemblies 120 are disposed within housing 140 and cover 142 is releasably securable to housing 140. When cover 142 is secured onto or over housing 140, housing 140 and cover 142 collectively define a rigid casing or enclosure that holds and protects sample holders 102 and bearing assemblies 120 therein. Housing 140 and cover 142 are preferably formed from a transparent material such as but not limited to acrylic or polycarbonate in order to allow the operator to see the internal components thereof. A plurality of tubular heaters 138 are attached or fixed to cover 142 by respective heater caps 139. In order to view the internal components of dilatation tester 100, heater caps 139 are not shown in FIG. 2 but are shown in FIG. 1 and FIG. 3. The number of heaters 138 is equal to the number of sample holders 102, and thus dilatation tester 100 includes four heaters 138 attached to and extending from an interior surface of cover 142. When cover 142 is disposed or secured onto or over housing 140 as best shown in FIG. 2 or FIG. 3, each heater 138 extends into a respective stent-graft prosthesis 108 received or disposed within a chamber of a respective sample holder 102. When disposed within a respective stent-graft prosthesis 108, an outer surface of heater 138 is spaced-apart from or separated by an annular space (not shown) from an inner surface of the stent-graft prosthesis 108. The annular space between a respective heater 138 and a respective stent-graft prosthesis 108 provides clearance between the two components such that heater 138 does not contact or provide support to the stent-graft prosthesis 108 as the stent-graft prosthesis 108 cyclically alternates between the loaded or compressed state and the unloaded or uncompressed state, as will be described in more detail herein. Heaters 138 maintain a temperature within housing 140 at 37° C. in order to mimic or simulate the temperature conditions of a stent-graft prosthesis disposed within a vasculature and further to expand the nitinol structures of the self-expanding stent-graft prosthesis. Fluid (not shown) is circulated into each heater 138 via inlet and outlet ports 150, 152, respectively, that extend through a respective heater cap 139 and are fluidly coupled to a heated fluid source (not shown) via suitable tubing (not shown) in order to ensure that the temperature within housing 140 remains constant at 37° C.

In another embodiment hereof, heaters 138 may be omitted and temperature controlled air may be circulated or cycled into chamber 106 of each sample holder 102 via inlet and outlet ports 150, 152 in order to ensure that the temperature within housing 140 remains constant at 37° C. The temperature controlled air may be circulated or cycled directly into chamber 106 of each sample holder 102, or may be circulated or cycled into a bladder or container (not shown) that is attached or fixed to cover 142 such that when cover 142 is disposed or secured onto or over housing 140 as best shown in FIG. 2 or FIG. 3, each bladder or container extends into a respective stent-graft prosthesis 108 received or disposed within a chamber of a respective sample holder 102. In this embodiment, air (not shown) is circulated into each chamber 106 via inlet and outlet ports 150, 152, respectively, that are fluidly coupled to a heated or temperature-controlled air supply (not shown) via suitable tubing (not shown). Outlet port 152 includes a check valve thereon (not shown) that is configured to allow flow in one direction, i.e., out of chamber 106, only. When compressible member 104 and the stent-graft prosthesis 108 therein are compressed, the temperature controlled air is forced out of each chamber 106 via outlet port 152 and warmer air is drawn into chamber 106 via inlet port 150 to form a built-in circulatory system. Stated another way, each sample holder 102 functions as a pump by expanding and compressing and thereby providing the energy for the required pressure to evacuate chamber 106 via outlet port 152. When compressible member 104 is compressed, the air within chamber 106 is forced out via outlet port 152. Conversely, when compressible member 104 expands, the check valve positioned within outlet port 152 does not allow the evacuated air to return into chamber 106 and thus warmer air is drawn into chamber 106 from the heated or temperature-controlled air supply via inlet port 150.

Figure 4:
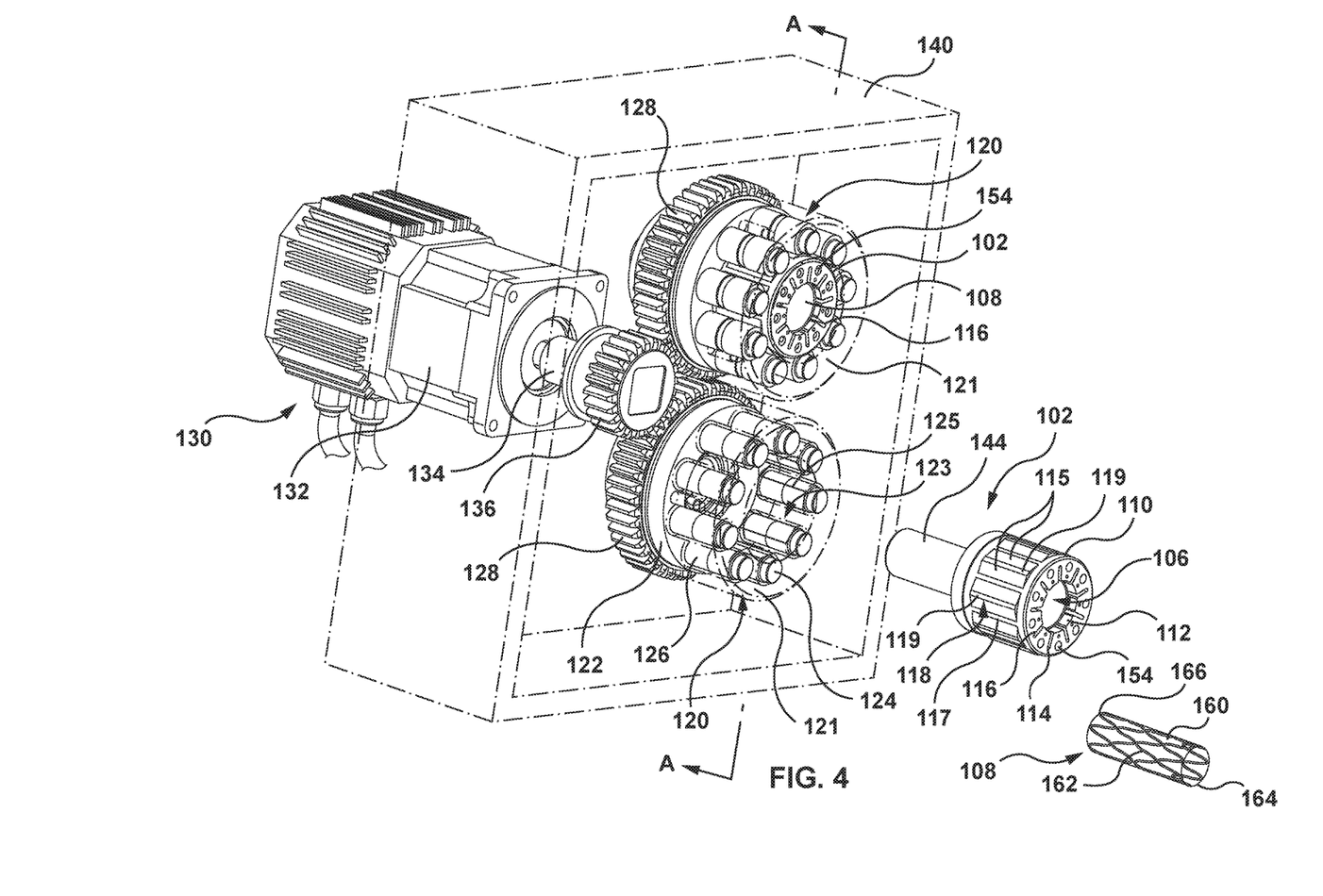
FIG. 4 is an exploded perspective view of the dilatation tester of FIG. 1 partially disassembled, wherein one sample holder is shown removed from its corresponding bearing assembly for illustrative purposes and one stent-graft prosthesis is shown removed from its corresponding sample holder for illustrative purposes.
Figure 5:
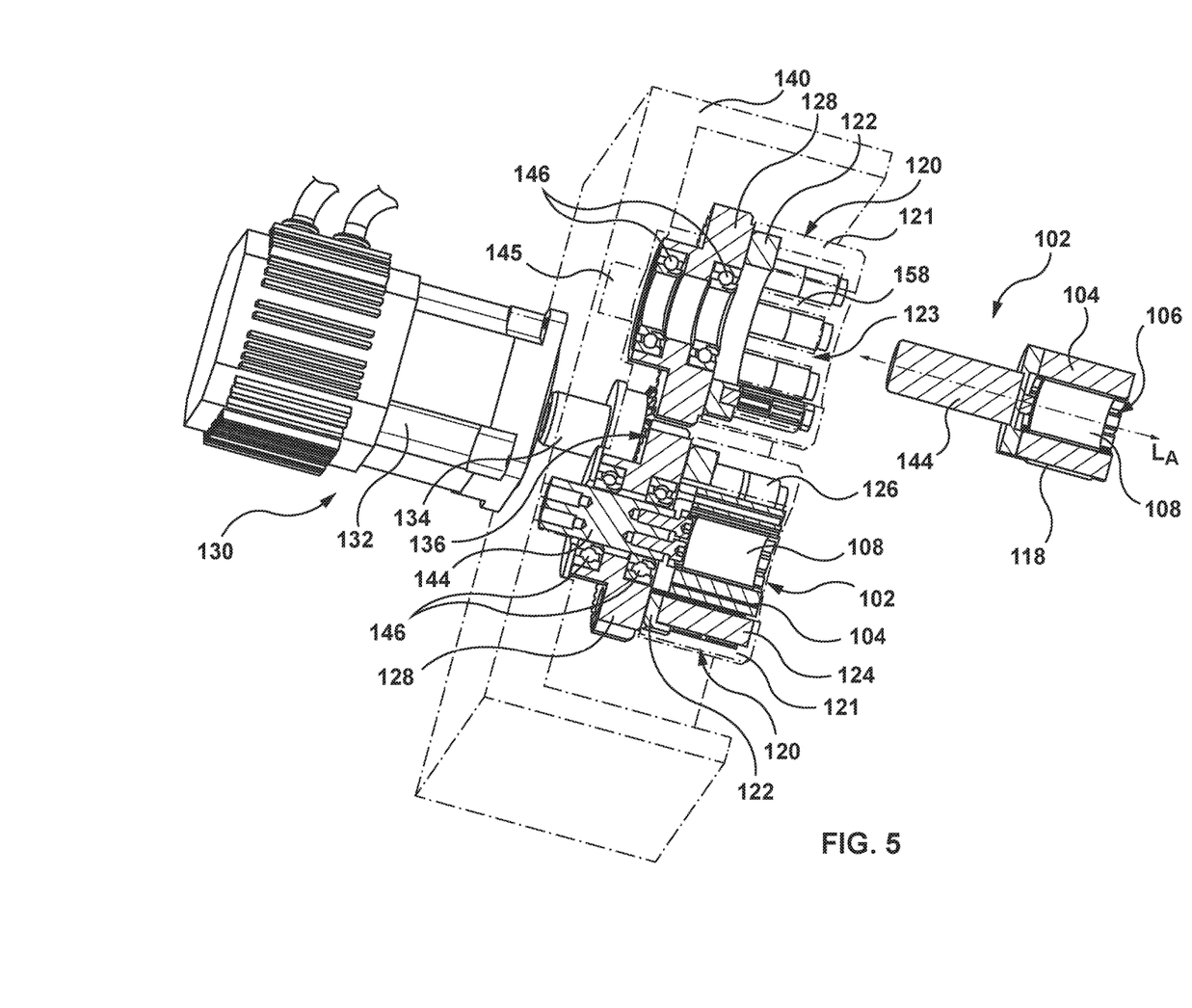
FIG. 5 is a cross-sectional view of FIG. 4 taken along a line A-A thereof.

With additional reference to FIGS. 3-5, sample holder 102 will be described in more detail. FIG. 3 is a cross-sectional view of FIG. 2, with heater caps 139 being shown in FIG. 3 but removed in FIG. 2 for sake of clarity. FIG. 4 is an exploded perspective view of a portion of dilatation tester 100 with one sample holder 102 being removed from housing 140 for illustrative purposes, and FIG. 5 is a cross-sectional view of FIG. 4. As best shown in the removed sample holder of FIGS. 4 and 5, each sample holder 102 includes a cylindrical base 144 and a compressible member 104 attached to cylindrical base 144. When assembled into housing 140, each cylindrical base 144 is disposed within a corresponding cavity 145 (see FIG. 3 and FIG. 5) in a floor of the housing and fixed or secured thereto so that sample holder 102 is not permitted to rotate during operation of dilatation tester 100. Cylindrical base 144 includes a plurality of positioning rods 156 (best shown in the cross-sectional view of FIG. 3) that are attached to and extend from cylindrical base 144 of sample holder 102 that is fixed to the housing. Compressible member 104 includes a plurality of bores or passageways 154 formed there-through and the plurality of positioning rods 156 are housed or received within the plurality of bores 154 in order to couple cylindrical base 144 and compressible member 104 together. More particularly, since cylindrical base 144 and positioning rods 156 extending therefrom are fixed to housing 140, bores 154 and positioning rods 156 housed therein prevent rotary motion or spinning of compressible member 104 with its respective bearing assembly 120 during operation of dilatation tester 100. Although each sample holder 102 illustrates nine bores 154 formed there-through, the number of bores 154 and positioning rods 156 housed therein may vary. In the longitudinal direction, i.e., in the direction of the longitudinal axis $L_A$ of sample holder 102 shown in FIG. 5, bores 154 and positioning rods 156 housed therein are of a length that extends the full length of compressible member 104.

As best shown on FIG. 3, cylindrical base 144 may also include a stabilization plate 143 which is positioned directly below chamber 106 defined by compressible member 104 and has a diameter equal to the size of chamber 106 when compressible member 104 is expanded. Stabilization plate 143 prevents each sample holder 902 from rocking, i.e., moving or translating from side to side, during rotary or spinning operation of bearing assemblies 120.

Compressible member 104 is formed from an elastomeric material such as but not limited to rubber or silicone. Compressible member 104 has an annular wall 114 defined between an exterior surface 110 and an interior surface 112 thereof. Interior surface 112 of compressible member 104 defines a chamber 106 of the sample holder that has an inner diameter that is suitably sized to receive stent-graft prosthesis 108 in an expanded state. Stated another way, when stent-graft prosthesis 108 is received within chamber 106 the stent-graft prosthesis expands into contact with interior surface 112 of compressible member 104. In an embodiment, the inner diameter of chamber 106 is configured to be approximately equal to a fully deployed or expanded diameter of stent-graft prosthesis 108, i.e., the fully deployed or expanded diameter of stent-graft prosthesis 108 when positioned in situ. In another embodiment, the inner diameter of chamber 106 may be chosen to be less than a fully expanded diameter of stent-graft prosthesis 108 such that the stent-graft prosthesis will be under a pre-load during testing. Stated another way, when disposed within chamber 108 with a relatively smaller inner diameter, stent-graft prosthesis 108 is under-expanded relative to its fully deployed or expanded diameter in order to apply a pre-load to the stent-graft prosthesis and thereby conservatively simulate loading forces.

Exterior surface 110 of compressible member 104 defines a plurality of longitudinally-extending raised surfaces or protuberances 118 that are separated or spaced apart by longitudinally-extending valleys 117. Protuberances 118 are evenly spaced about or around a circumference of the compressible member and each protuberance 118 radially aligns with a respective radially-extending slot 116 of compressible member 104, as described below. Although compressible member 104 includes nine protuberances 118 and nine corresponding slots 116, a compressible member in accordance herewith may include more or fewer such features without departing from a scope of the present invention as long as an equal number of each are present.

As best shown in the exploded view of FIG. 4, each protuberance 118 is a raised feature or bump that has a frusta-conical profile and includes a flat planar surface or plateau 119 having inclined or ramped surfaces 115 on each side thereof. In an embodiment, each protuberance may have a height determined by the following equation: $H=(D*\% Dilatation)/2$, with H being the height of a protuberance measured relative to one of the valleys 117 on either side thereof and D being the diameter of the stent-graft prosthesis. As will be explained in more detail herein, protuberances 118 operate similar to cams during operation of dilatation tester 100 and the height thereof may be varied to change the load on a stent-graft prosthesis received therein. Further, the profile of protuberances 118 can be changed to generate different pulse shapes. In a longitudinal direction, i.e., in the direction of the longitudinal axis $L_A$ of sample holder 102 shown in FIG. 5, protuberances 118 may have a length that extends substantially a full length of chamber 106 of compressible member 104. In another embodiment, protuberances 118 may extend between 75% and 100% of a length of chamber 106.

Radially-extending slots 116 of compressible member 104 are evenly spaced relative to a circumference of compressible member 104 and radially extend from interior surface 112 toward exterior surface 110, and more particularly toward a respective protuberance 118 thereof. Each radially-extending slot 116 may have a depth of between 40-80% of a thickness of annular wall 114. In the longitudinal direction, i.e., in the direction of the longitudinal axis $L_A$ of sample holder 102 shown in FIG. 5, radially-extending slots 116 may have a length that extends substantially a full length of chamber 106 of compressible member 104. In embodiments hereof, each radially-extending slot 116 may have a width up to 0.070 inches.

Bearing assemblies 120 are concentrically disposed about compressible members 104 of sample holders 102, such that a plurality of needle roller bearings 126 of a respective bearing assembly 120 contact and act on the exterior surface 110 of a corresponding compressible member 104. As previously stated, the number of bearing assemblies corresponds to the number of sample holders. Each bearing assembly 120 includes an annular base 122, a plurality of dowel pins or rods 124, and a plurality of needle roller bearings 126. The annular base 122 of each bearing assembly 120 is fixed or secured to a dedicated or external gear 128 so that during operation of dilatation tester 100 the bearing assembly 120 rotates with the external gear 128 relative to its sample holder 102, as will be explained in more detail herein. The plurality of dowel pins 124 are attached to annular base 122 to extend therefrom and to receive the plurality of needle roller bearings 126 thereon such that a respective needle roller bearing 126 is rotatable about a respective dowel pin 124. In an embodiment hereof, each needle roller bearing 126 may be a Teflon sleeve that is mounted to be rotatable about a respective dowel pin 124.

Annular base 122, the plurality of dowel pins 124, and the plurality of needle roller bearings 126 are housed or disposed within an annular bearing housing 121 that includes a plurality of corresponding bearing openings or windows 125 (best shown in FIG. 2) formed through bearing housing 121. The inner surface of bearing housing 121 defines a cylindrical space 123 configured to receive sample holder 102. Windows 125 are evenly spaced relative to a circumference of bearing housing 121, with dowel pins 124 being attached to bearing housing 121 such that needle roller bearings 126 are disposed or installed within windows 125. More particularly, a respective dowel pin 124 extends between and is secured at top and bottom ends of the bearing housing 121 within a respective window 125 with a respective needle roller bearing 126 disposed thereover to laterally extend from the respective window 125 of bearing housing 121. Each needle roller bearing 126 freely rolls or spins about its respective dowel pin 124 within its respective window 125 without contacting bearing housing 121. As best shown in FIGS. 4 and 5 with bearing assembly 120 having sample holder 102 removed therefrom, each needle roller bearing 126 has an outer diameter greater than a wall thickness of annular bearing housing 121. Thus, when disposed or installed within windows 125 of the bearing housing, needle roller bearings 126 extend or are disposed slightly radially inward of the inner surface of bearing housing 121 and extend or are disposed slightly radially outward of an outer surface of bearing housing 121. Stated another way, needle roller bearings 121 are wider than the wall of bearing housing 121 and windows 125 are sized such that needle roller bearings 121 make no rolling contact with bearing housing 121.

When a sample holder 102 is disposed within a respective cylindrical space 123 of a respective bearing housing 121, the plurality of needle roller bearings 126 surround and continuously make contact with the exterior surface 110 of a respective compressible member 104 of the sample holder 102. More particularly, bearing assembly 120 and compressible member 104 are concentric and thus have a common axis, and are disposed relative to each other such that the needle roller bearings 126 may roll over the exterior surface 110 of compressible member 104 during operation of dilatation tester 100. During operation of dilatation tester 100, as will be explained in more detail herein with respect to FIGS. 6 and 7, bearing assembly 120 is rotated with respect to sample holder 102 such that stent-graft prosthesis 108 is radially compressed or subjected to a load every time the plurality of needle roller bearings 126 of bearing assembly 120 and the plurality of protuberances 118 of sample holder 102 are aligned and is uncompressed or unload every time the plurality of needle roller bearings 126 of bearing assembly 120 and the plurality of valleys 117 of sample holder 102 are aligned. Needle roller bearings 126 operate similar to cam followers during operation of dilatation tester 100 and the amount of radial compression of compressible member 104 may be dependent upon the diameter of needle roller bearings 126. Stated another way, in an embodiment the amount of radial compression of compressible member 104 may be dependent upon the diameter of needle roller bearings 126 and thus the loading forces applied to the stent-graft prosthesis may be varied by changing the size of the needle roller bearings. Similarly, in another embodiment, the amount of radial compression of compressible member 104 may be dependent upon the diameter of compressible member 104 and thus the loading forces applied to the stent-graft prosthesis may be varied by changing the size of the compressible member. The number of needle roller bearings 126 of each respective bearing assembly 120 is equal to the number of protuberances 118 (and thus is also equal to the number of radially-extending slots 116) of a respective compressible member 104. Thus, although bearing assembly 120 illustrates nine needle roller bearings 126 included therein, the number of needle roller bearings 126 may vary so long as the number of needle roller bearings 126 is equal to the number of protuberances 118.

Notably, needle roller bearings 126, protuberances 118, and radially-extending slots 116 extend the full length or most of the full length of compressible member 104 and stent-graft prosthesis 108 received therein. Accordingly, when the plurality of needle roller bearings 126 and the plurality of protuberances 118 simultaneously or concurrently align to cause radial compression of compressible member 104 and stent-graft prosthesis 108 received therein, the longitudinal dimensions of needle roller bearings 126, protuberances 118, and radially-extending slots 116 ensure that the full length of compressible member 104 and stent-graft prosthesis 108 received therein is simultaneously radially compressed from each direction about the entire circumference thereof. Stated another way, the longitudinal dimensions result in radial compression of stent-graft prosthesis 108 along the full length thereof from first end 164 to second end 166 about the entire perimeter of the stent-graft prosthesis. As such, the cyclical radial compression of stent-graft prosthesis 108 mimics or simulates loading of a stent-graft prosthesis implanted within a vasculature due to a beating heart in order to test stent-graft prosthesis 108 according to industry standards.

As previously mentioned, dilatation tester 100 includes actuation assembly 130 operably coupled to bearing assembly 120 for rotating the bearing assembly relative to sample holder 102. Actuation assembly 130 includes a motor 132 having a shaft 134. While motor 132 is external to housing 104, shaft 134 extends within housing 104 and is coupled to a central or driving gear 136 as best shown in FIG. 4. Driving gear 126 meshes with each dedicated or external gear 128 attached to a corresponding bearing assembly 120 such that when motor 132 is operated the corresponding rotation of shaft 134 and driving gear 136 drives each dedicated or external gear 128 to thereby rotate the corresponding bearing assembly 120 relative to the corresponding sample holder 102. As will be understood by one of ordinary skill in the art, driving gear 136 and dedicated or external gears 128 are not required when the dilatation tester includes only one sample holder and one corresponding bearing assembly because motor 132 and shaft 134 may directly drive the single bearing assembly. However, when the dilatation tester includes multiple sample holders and corresponding bearing assemblies, the gear assembly is provided such that a single motor, i.e., motor 132, can drive multiple bearing assemblies 120. Motor 132 may include a counter (not shown) in order to count revolutions thereof so that an operator may track corresponding cycles of the dilatation tester.

In an embodiment hereof, bearing assemblies 120 may be configured to be out of phase with each other in order to reduce or minimize the amount of torque required by motor 132. More particularly, bearing assemblies 120 are configured such that two of the four bearing assemblies 120 are positioned over inclined surfaces 115 of protuberances 118, i.e., the surfaces leading up to or positioned before plateaus 119, of two respective sample holders 102 while the remaining two bearing assemblies 120 are positioned over opposing ramped surfaces 115 of protuberances 118, i.e., the surfaces following or positioned after plateaus 119, of the remaining two respective sample holders 102.

As best shown in the cross-sectional view of FIG. 3, each dedicated or external gear 128 of a respective bearing assembly 120 is also attached to a respective cylindrical base 144 of sample holder 102 via a plurality of roller bearings 146. Roller bearings 146 allow dedicated or external gear 128 to rotate around or relative to cylindrical base 144 of sample holder 102 which is fixed or secured to housing 140. More particularly, each cylindrical base 144 of a respective sample holder 102 is fixed within a corresponding cavity 145 in a floor of housing 140 so that the sample holder 102 is not permitted to rotate with external gear 128. Thus, sample holders 102 remain stationary during operation of dilatation tester 100 while each dedicated or external gear 128 and respective bearing assembly 120 rotates relative to the respective sample holder 102 and stent-graft prosthesis 108 received therein.

Figure 10:
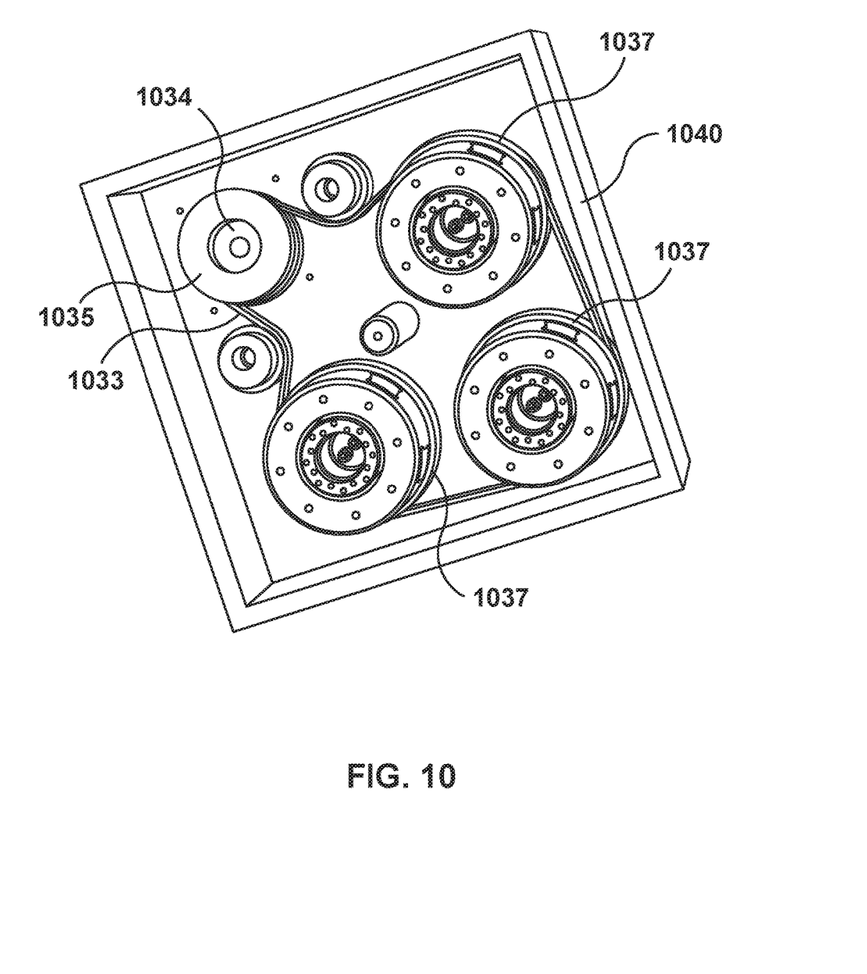
FIG. 10 is a perspective view of another embodiment of a dilatation tester, wherein the dilatation tester includes a timing belt drive system and a cover of the dilatation tester is shown removed from a housing of the dilatation tester to illustrate the internal components of the dilatation tester.

Although shown with a gear assembly including driving gear 136 and dedicated or external gears 128 for providing rotational energy to sample holders 102, it will be understood by one of ordinary skill in the art that alternative drive systems may be utilized herein to rotate bearing assembly 120 relative to the respective sample holder 102 and stent-graft prosthesis 108 received therein. For example, as shown in FIG. 10, rotational energy may be provided to a plurality of sample holders via a single motor (not shown in FIG. 10) having a shaft 1034 and a timing belt drive system that includes a flexible belt 1033, a driving pulley 1035, and a plurality of dedicated or external pulleys 1037. Similar to the motor 132, the motor of FIG. 10 is external to housing 1040 and shaft 1034 extends within housing 1040 and is coupled to driving pulley 1035. Each dedicated or external pulley 1037 is attached to a corresponding bearing assembly such that when the motor is operated the corresponding rotation of shaft 1034 and driving pulley 1035 drives belt 1033 and each dedicated or external pulley 1037 to thereby rotate the corresponding bearing assembly relative to the corresponding sample holder and stent-graft prosthesis received therein. Belt 1033 may include teeth (not shown) on an inside surface thereof that are configured to match or mate with teeth (not shown) on outside surfaces of pulleys 1035, 1037 is order to prevent slippage between the components.

Figure 6:
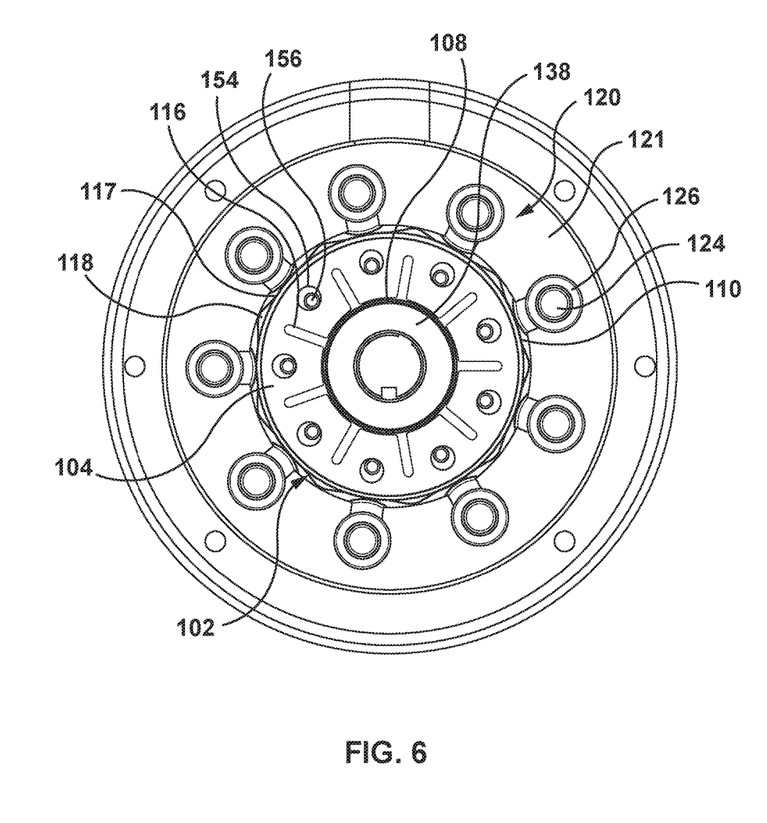
FIG. 6 is a top view of a sample holder and corresponding bearing assembly of the dilatation tester of FIG. 1, wherein the sample holder and corresponding bearing assembly are removed from the housing of the dilatation tester for illustrative purposes only and a stent-graft prosthesis received within the sample holder is an uncompressed or unloaded state.
Figure 7:
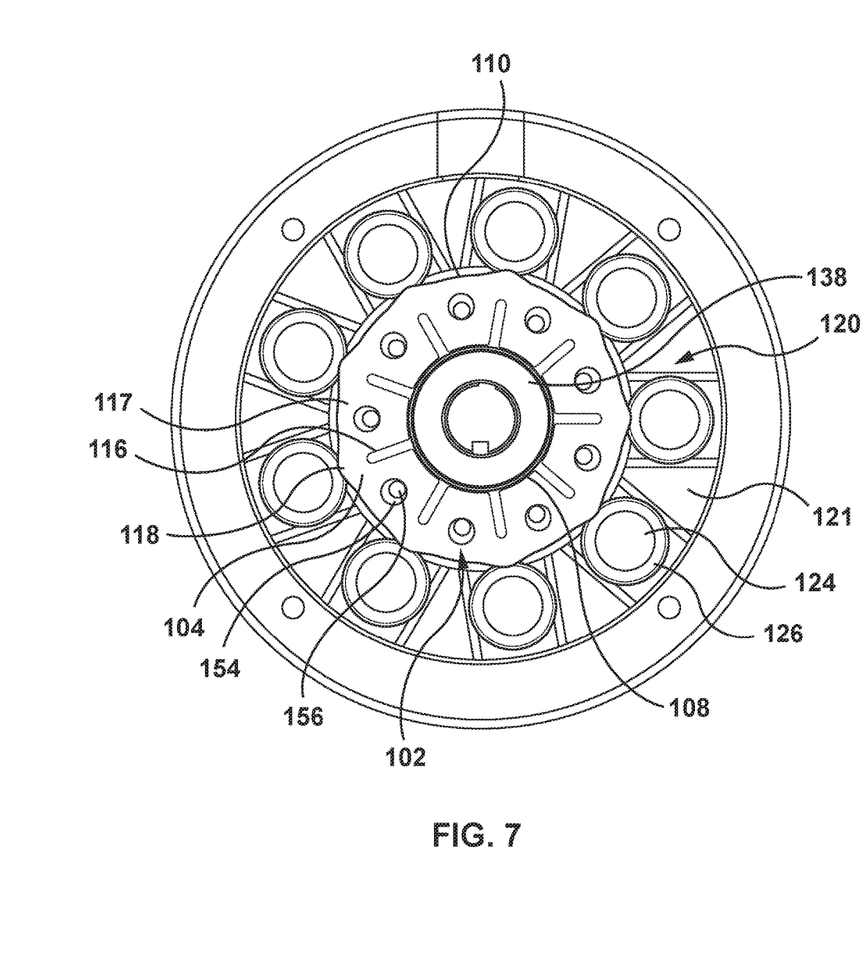
FIG. 7 is a cross-sectional view of a sample holder and corresponding bearing assembly of the dilatation tester of FIG. 1, wherein the sample holder and corresponding bearing assembly are removed from the housing of the dilatation tester for illustrative purposes only and a stent-graft prosthesis received within the sample holder is in a radially compressed or loaded state.

Operation of dilatation tester 100 will now be described in more detail with additional reference to FIGS. 6 and 7. FIG. 6 is a top view of a sample holder 102 and corresponding bearing assembly 120 removed from housing 140 of dilatation tester 100 for illustrative purposes only, with stent-graft prosthesis 108 received within the sample holder 102 being in an uncompressed or unloaded state. FIG. 7 is a cross-sectional view of a sample holder 102 and corresponding bearing assembly 120 removed from housing 140 of dilatation tester 100 for illustrative purposes only, with stent-graft prosthesis 108 received within the sample holder 102 being in a compressed or loaded state.

As shown in FIG. 6, stent-graft prosthesis 108 is received within sample holder 102 in an expanded state such that stent-graft prosthesis 108 received within the sample holder expands into contact with interior surface 112 of compressible member 104. As previously explained, in an embodiment, the inner diameter of chamber 106 may be configured to be less than a fully expanded diameter of stent-graft prosthesis 108 such that the stent-graft prosthesis will be under a pre-load during testing. In another embodiment, the inner diameter of chamber 106 is configured to be approximately equal to a fully expanded diameter of stent-graft prosthesis 108. Tubular heater 138 is disposed within stent-graft prosthesis 108 in order to maintain a temperature of 37° C. as described above. In FIG. 6, the plurality of needle roller bearings 126 of bearing assembly 120 are radially aligned and in contact with the plurality of valleys 117 of compressible member 104. Since protuberances 118 are not in contact with needle roller bearings 126, compressible member 104 is not compressed and stent-graft prosthesis 108 disposed within compressible member 104 is in an uncompressed or unloaded state.

During operation, needle roller bearings 126 maintain contact with exterior surface 110 of compressible member 104 at all times and compressible member 104 makes no direct contact with bearing housing 121. Needle roller bearings 126 roll over exterior surface 110 of compressible member 104, and compressible member 104 is cyclically compressed as needle roller bearings 126 roll over protuberances 118. More particularly, when bearing assembly 120 is rotated via actuation assembly 130, sample holder 102 remains stationary and bearing assembly 120 moves or rotates relative to compressible member 104. When bearing assembly 120 is being rotated via actuation assembly 130, each needle roller bearing 126 rolls or spins about its respective dowel pin 124. Accordingly during each complete revolution of bearing assembly 120 about compressible member 114, the plurality of needle roller bearings 126 will concurrently or simultaneously be positioned over or aligned with the plurality of protuberances 118 of compressible member 104 as shown in FIG. 7 nine times. Each time needle roller bearings 126 and protuberances 118 are aligned, compressible member 104 of sample holder 102 as well as stent-graft prosthesis 108 received therein are radially compressed. In addition to permit greater compression when aligned, needle roller bearings 126 act on or push inward on protuberances 118 of compressible member 104 and in turn elastically deform the plurality of radially-extending slots 116 of compressible member 104 which are also aligned with protuberances 118. Due to elastic deformation of radially-extending slots 116, as well as the elastomeric material thereof, compressible member 104 is radially compressed each time the plurality of protuberances 118 are aligned with the plurality of needle roller bearings 126 during the rotation or revolution of the bearing assembly thereabout. The plurality of radially-extending slots 116 are aligned with protuberances 118 in order to ensure that compressible member 104 is compressed in a uniform manner. When the plurality of needle roller bearings 126 contact protuberances 118, the plurality of needle roller bearings 126 collectively and simultaneously push protuberances 118 radially inward and deform the plurality of radially-extending slots 116 such that compressible member 104 is radially compressed in a uniform manner towards the longitudinal axis.

As needle roller bearings 126 roll or move over protuberances 118, protuberances 118 operate similar to cams that strike or contact the needle roller bearings (which operate similar to cam followers) at particular points or positions on a circular path. The height of protuberances 118 and/or the diameter of needle roller bearings 126 may be varied in order to change loads, i.e., change the amount of radial compression, subjected onto stent-graft prosthesis 108. For example, increasing the height of protuberances 118 and/or the diameter of needle roller bearings 126 results in more radial compression of compressible member 104 and stent-graft prosthesis 108 received therein while decreasing the height of protuberances 118 and/or the diameter of needle roller bearings 126 results in less radial compression of compressible member 104 and stent-graft prosthesis 108 received therein.

As bearing assembly 120 is continuously rotated via actuation assembly 130, needle roller bearings 126 continuously roll over exterior surface 110 of compressible member 104. Needle roller bearings 126 contact or act on inclined or ramped surfaces 115 of protuberances 118 to cyclically compress compressible member 104, thereby providing cyclic loading and unloading of stent-graft prosthesis 108 disposed within compressible member 104. Stent-graft prosthesis 108 is loaded or compressed each time the plurality of needle roller bearings 126 are radially aligned with the plurality of protuberances 118 of compressible member 104, and stent-graft prosthesis 108 is unloaded or uncompressed each time the plurality of needle roller bearings 126 are radially aligned with the plurality of valleys 117 of compressible member 104. Cyclical loading and unloading of stent-graft prosthesis 108 mimics or simulates physiologic loading conditions of a stent-graft prosthesis within a vasculature due to a beating heart. More particularly, diastole or diastolic blood pressure is simulated when needle roller bearings 126 are aligned with valleys 117 of compressible member 104 and stent-graft prosthesis 108 is in an uncompressed or unloaded state as shown in FIG. 6. Systole or systolic blood pressure is simulated when needle roller bearings 126 are aligned with protuberances 118 and stent-graft prosthesis 108 is in a compressed or loaded state as shown in FIG. 7. Due to nine total pairs of needle roller bearings 126 and protuberances 118, one complete rotation or turn of bearing assembly 120, or stated another way a single cycle of bearing assembly 120 relative to sample holder 102, radially compresses compressible member 104 and stent-graft prosthesis 108 received therein nine times. In an embodiment, actuation assembly 130 rotates bearing assembly 120 at a frequency up to 150 Hz or 9000 cycles per minute.

Figure 8:
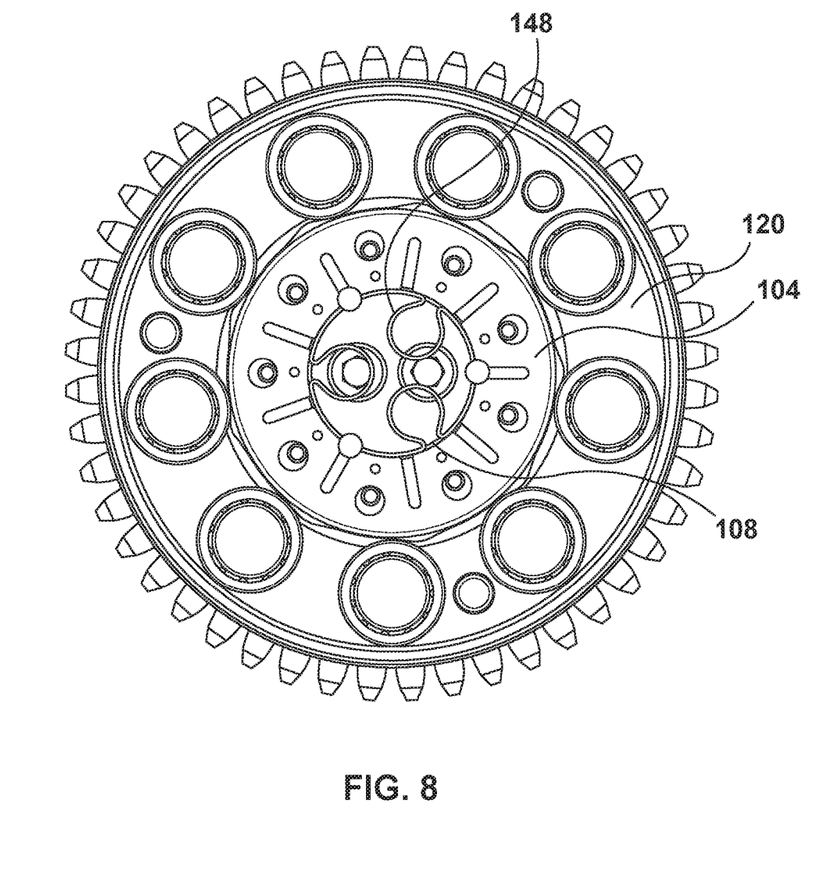
FIG. 8 is a top view of a sample holder and corresponding bearing assembly of the dilatation tester of FIG. 1, wherein the sample holder and corresponding bearing assembly are removed from the housing of the dilatation tester for illustrative purposes only and a measurement fixture is shown received within a mouth of the sample holder.

Turning to FIG. 8, dilatation tester 100 may include a measurement fixture 148 for measuring or determining the amount of radial compression or dilatation of compressible member 104 and stent-graft prosthesis 108 received therein. FIG. 8 is a top view of a sample holder and corresponding bearing assembly of the dilatation tester of FIG. 1, wherein the sample holder and corresponding bearing assembly are removed from the housing of the dilatation tester for illustrative purposes only and a measurement fixture is shown disposed spanning a mouth of the chamber 106 of the sample holder. Measurement fixture 148 triangulates the distance traveled by the inner diameter of compressible member 104 in order to determine the amount of radial compression or dilatation of compressible member 104 and stent-graft prosthesis 108 received therein.

Figure 9:
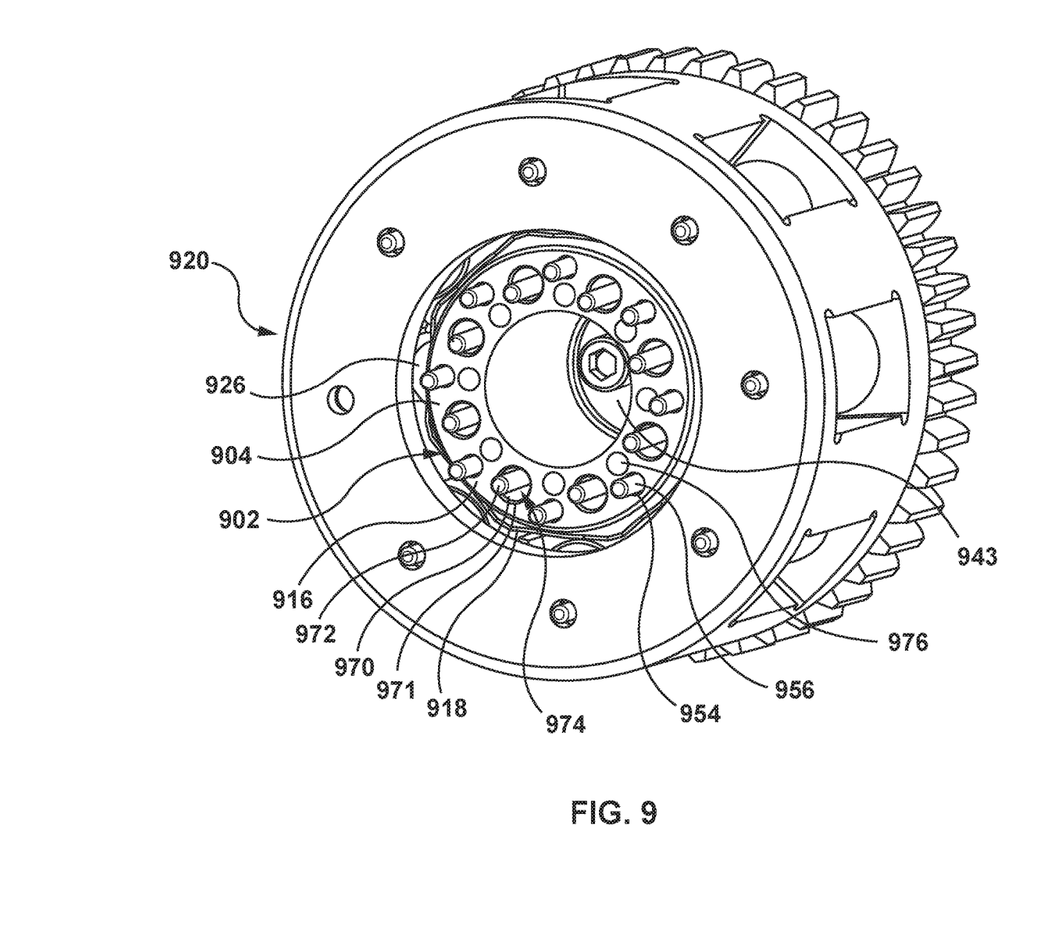
FIG. 9 is a perspective view of a sample holder and corresponding bearing assembly according to another embodiment hereof, wherein the sample holder includes a compressible member having a plurality of tubes and stabilization pins housed therein for ensuring uniform radial compression of the compressible member.

FIG. 9 illustrates a sample holder 902 and a corresponding bearing assembly 920 according to another embodiment hereof. Similar to above, sample holder 902 receives a stent-graft prosthesis (not shown in FIG. 9) in an expanded state and bearing assembly 920 rotates relative to and acts on sample holder 902 in order to provide cyclical radial compression of the stent-graft prosthesis received therein. In this embodiment, however, a compressible member 904 of sample holder 902 does not include radially-extending slots in order to ensure that the compressible member and stent-graft prosthesis are compressed in a uniform manner. Rather, compressible member 904 includes a plurality of bores or channels 971 formed through an annular wall 916 of compressible member 904 which provide compressible member 904 with the flexibility, compressibility, and compliance required in order to radially compress. A thin-walled tube 970 extends through each bore or channel 971. Each tube 970 may be formed from stainless steel or a similar material. The plurality of bores or channels 971 and tubes 970 housed therein are evenly spaced relative to a circumference of compressible member 904 and are radially aligned with a plurality of longitudinally-extending raised surfaces or protuberances 918 formed on the exterior surface of compressible member 904, which are similar to protuberances 118 described above. In the longitudinal direction, the plurality of bores or channels 971 and tubes 970 housed therein have a length that extends a full length of compressible member 904.

A plurality of stabilization pins 972 may be housed within the plurality of tubes 970. An outer diameter of each stabilization pin 972 is less than an inner diameter of a respective tube 970 such that a clearance space or gap 974 extends between the tube 970 and respective stabilization pin 972 to permit radial compression of compressible member 904 during operation. Each stabilization pin 972 is attached to and extends from a stabilization plate 943 of sample holder 902, which is similar to stabilization plate 143 of sample holder 102 described above. Stabilization plate 943 and stabilization pins 972 prevent each sample holder 902 from rocking, i.e., moving or translating from side to side, during rotary or spinning operation of bearing assemblies 920.

Similar to sample holder 102, sample holder 902 also includes a plurality of bores or passageways 954 formed through compressible member 904 and a plurality of positioning rods 956 housed within the plurality of bores 954 in order to prevent rotary motion or spinning of compressible member 904 with its respective bearing assembly 920 during operation of the dilatation tester. Further, sample holder 902 further includes another set of bores or hollow channels 976 that do not house any tubes, rods, pins, or other structures. Rather, hollow channels 976 are provided to increase the flexibility of compressible member 904 and provide the compressible member with additional compressibility and compliance. Although hollow channels 976 are shown with a circular cross-section, the cross-sectional shape or configuration of hollow channels 976 may vary. For example, hollow channels 976 may for example have a keyhole cross-sectional shape or configuration (not shown) with a circular portion and a slot or rectangular portion that extends from the circular portion to the inner surface of the compressible member.

In order to permit compression when aligned, needle roller bearings 926 of bearing assembly 920 act on or push inward on protuberances 918 of compressible member 904 and in turn elastically deform compressible member 904. Due to elastic deformation of hollow channels 976 of compressible member 904, compressible member 904 is radially compressed each time the plurality of protuberances 918 are aligned with the plurality of needle roller bearings 926 during the rotation or revolution of the bearing assembly thereabout. When the plurality of needle roller bearings 926 contact protuberances 918, the plurality of needle roller bearings 926 collectively or simultaneously push protuberances 918 radially inward such that compressible member 904 is radially compressed in a uniform manner towards the longitudinal axis. Bores or channels 971, which provide compressible member 904 with the flexibility, compressibility, and compliance required in order to radially compress, are aligned with protuberances 918 in order to ensure that compressible member 904 is compressed in a uniform manner. The plurality of tubes 970 housed within bores 971 provide the required stiffness to ensure that the inner surface or diameter of compressible member 904 radially compresses, or stated another way, tubes 970 prevent collapse of bores or channels 971 when the plurality of needle roller bearings 926 collectively or simultaneously push protuberances 918 radially inward.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A dilatation tester for a stent-graft prosthesis comprising:
 a sample holder having a compressible member that defines a chamber for receiving a stent-graft prosthesis in an expanded state;
 a bearing assembly disposed to contact an exterior surface of the compressible member of the sample holder; and
 an actuation assembly operably coupled to the bearing assembly for rotating the bearing assembly relative to the sample holder, wherein rotation of the bearing assembly cyclically compresses the compressible member of the sample holder to thereby provide cyclical radial compression of a stent-graft prosthesis received therein for simulating physiologic loading conditions of a stent-graft prosthesis within a vasculature due to a beating heart.

2. The dilatation tester of claim 1, wherein the exterior surface of the compressible member defines a plurality of longitudinally-extending protuberances evenly spaced about a circumference of the compressible member.

3. The dilatation tester of claim 2, wherein rotation of the bearing assembly cyclically compresses the compressible member when a plurality of needle roller bearings of the bearing assembly roll over and radially compress the plurality of longitudinally-extending protuberances.

4. The dilatation tester of claim 3, wherein the compressible member has an annular wall defined between the exterior surface and an interior surface thereof that includes a plurality of radially-extending slots formed therein and wherein each of the plurality of radially-extending slots aligns with a respective raised surface of the plurality of longitudinally-extending protuberances of the compressible member.

5. The dilatation tester of claim 3, wherein the compressible member includes a plurality of bores extending through an annular wall defined between the exterior surface and an interior surface thereof and wherein each of the plurality of bores aligns with a respective raised surface of the plurality of longitudinally-extending protuberances of the compressible member.

6. The dilatation tester of claim 3, wherein an interior surface of the compressible member defines the chamber of the sample holder and wherein a stent-graft prosthesis received within the chamber expands into contact with the interior surface of the compressible member.

7. The dilatation tester of claim 1, further comprising:
a tubular heater that is sized to be disposed within a stent-graft prosthesis received within the chamber of the sample holder.

8. The dilatation tester of claim 7, further comprising:
a housing within which the sample holder and the bearing assembly are disposed; and
a cover that is releasably securable to the housing, wherein the tubular heater is fixed to the cover to extend within the sample holder when the cover is secured to the housing.

9. The dilatation tester of claim 8, wherein the actuation assembly includes a motor and a shaft of the motor extends within the housing and is coupled to a driving gear, and wherein the driving gear meshes with a dedicated gear attached to the bearing assembly such that when the motor is operated rotation of the shaft and the driving gear drives the dedicated gear to thereby rotate the bearing assembly relative to the sample holder.

10. The dilatation tester of claim 9, wherein the bearing assembly is comprised of
an annular base, a plurality of dowel pins and a plurality of needle roller bearings, wherein the plurality of dowel pins are attached to the annular base to extend therefrom and to receive the plurality of needle roller bearings thereon such that a respective needle roller bearing is rotatable about a respective dowel pin.

11. The dilatation tester of claim 10, wherein the annular base of the bearing assembly is fixed to the dedicated gear.

12. The dilatation tester of claim 11, wherein the sample holder includes a cylindrical base that is fixed to the housing and wherein the dedicated gear is attached by one or more roller bearings to the cylindrical base of the sample holder.

13. The dilatation tester of claim 10, wherein the plurality of needle roller bearings surround and make contact with the compressible member of the sample holder.

14. The dilatation tester of claim 9, wherein the housing includes two or more sample holders and corresponding bearing assemblies and wherein the driving gear of the actuation assembly meshes with each dedicated gear attached to a respective bearing assembly of the two or more bearing assemblies.

15. The dilatation tester of claim 8, wherein the tubular heater maintains a temperature within the housing at 37° C.

16. A dilatation tester for a stent-graft prosthesis comprising:
a sample holder having a compressible member that defines a chamber for receiving a stent-graft prosthesis in an expanded state, wherein an exterior surface of the compressible member defines a plurality of longitudinally-extending protuberances evenly spaced about a circumference of the compressible member;
a bearing assembly including a plurality of needle roller bearings that surround and make contact with the exterior surface of the compressible member of the sample holder; and
an actuation assembly operably coupled to the bearing assembly for rotating the bearing assembly relative to the sample holder, wherein rotation of the bearing assembly cyclically compresses the compressible member when the plurality of needle roller bearings of the bearing assembly roll over and radially compress the plurality of longitudinally-extending protuberances of the compressible member of the sample holder to thereby provide cyclical radial loading and unloading of a stent-graft prosthesis received therein for simulating physiologic loading conditions of a stent-graft prosthesis within a vasculature due to a beating heart.

17. The dilatation tester of claim 16, wherein the compressible member has an annular wall defined between the exterior surface and an interior surface thereof that includes a plurality of radially-extending slots formed therein and each of the plurality of radially-extending slots of the compressible member aligns with a respective raised surface of the plurality of longitudinally-extending protuberances of the compressible member.

18. The dilatation tester of claim 16, wherein the compressible member includes a plurality of bores extending through an annular wall defined between the exterior surface and an interior surface thereof and wherein each of the plurality of bores aligns with a respective raised surface of the plurality of longitudinally-extending protuberances of the compressible member.

19. A dilatation tester for a stent-graft prosthesis comprising:
a sample holder having a compressible member that defines a chamber for receiving a stent-graft prosthesis in an expanded state, wherein an exterior surface of the compressible member defines a plurality of longitudinally-extending protuberances evenly spaced about a circumference of the compressible member;
a bearing assembly including a plurality of needle roller bearings that surround and make contact with the exterior surface of the compressible member of the sample holder; and
an actuation assembly operably coupled to the bearing assembly for rotating the bearing assembly relative to the sample holder, wherein the compressible member and a stent-graft prosthesis received therein are radially compressed when the plurality of longitudinally-extending protuberances of the compressible member are aligned with the plurality of needle roller bearings of the bearing assembly.

20. The dilatation tester of claim 19, wherein the compressible member is not radially compressed and the stent-graft prosthesis is in the expanded state when the plurality of needle roller bearings of the bearing assembly are aligned with a plurality of longitudinally-extending valleys that are disposed between the plurality of longitudinally-extending protuberances of the compressible member.

* * * * *